United States Patent [19]

Barry et al.

[11] Patent Number: 5,574,145
[45] Date of Patent: Nov. 12, 1996

[54] ISOLATED NUCLEIC ACID MOLECULES TARGETED TO THE REGION INTERMIDIATE TO THE 16S AND 23S rRNA GENES USEFUL AS PROBES FOR DETERMINING BACTERIA

[75] Inventors: Thomas G. Barry, County Galway; Bernard F. X. Gannon; Richard Powell, both of Galway, all of Ireland

[73] Assignees: Bioresearch Ireland, Dublin; University College Galway, Galway, both of Ireland

[21] Appl. No.: 173,639

[22] Filed: Dec. 22, 1993

Related U.S. Application Data

[62] Division of Ser. No. 830,465, Feb. 6, 1992, abandoned, which is a continuation of Ser. No. 510,853, Apr. 18, 1990, abandoned.

[30] Foreign Application Priority Data

Apr. 20, 1989 [IE] Ireland ..................................... 1287/89

[51] Int. Cl.$^6$ ....................................................... C07H 21/04
[52] U.S. Cl. .......................... 536/24.32; 435/6; 536/24.33
[58] Field of Search ................................ 536/23.1, 24.32, 536/24.33

[56] References Cited

U.S. PATENT DOCUMENTS

| | | | |
|---|---|---|---|
| 4,683,195 | 7/1987 | Mullis et al. ................................ | 435/6 |
| 4,851,330 | 7/1989 | Kohne ........................................ | 435/6 |

FOREIGN PATENT DOCUMENTS

| | | |
|---|---|---|
| 0335633 | 10/1989 | European Pat. Off. . |
| 2636075 | 3/1990 | France . |
| 8803957 | 6/1988 | WIPO . |
| 89/06704 | 7/1989 | WIPO . |

OTHER PUBLICATIONS

Zinsser: Microbiology, Nineteenth Edition, 1988). p. 450.
Engelke et al. Proc Natl Acad Sci USA (1988) 85: 544–548.
Dams et al. Nucl. Acids Res, (1988) 16 (Supplement) r87–r173.
Chen et al, Chemical Abstracts, vol. 110, No. 7, Abstract No. 149158e, p. 230 (1989).
Edwards et al, Nucleic Acids Research, vol. 17, No. 19, pp. 7843–7853 (1989).
Barry et al, Bio/Technology, vol. 8, pp. 233–236 (1990).
Woese, Scientific American, vol. 244 (6) pp. 94–106 (1981).
Maniatis et al, Molecular Cloning—A Laboratory Manual, Cold Spring Harbor Laboratory, pp. 310–328 (1982).
Saiki et al, Science, vol. 230, pp. 1350–1354 (1985).
Chen et al, FEMS Microbiology Letters, vol. 57, pp. 19–24 (1989).
Medlin et al, Gene, vol. 71, pp. 491–499 (1988).
Göbel et al., *J. Gen. Micro.* 133, 1969–1974 (1987).
Haun et al., *FEMS Micro. Lett.* 43, 187–193 (1987).
Suzuki et al., *J. Bacter.* 170(6), 2886–2889 (1988).

*Primary Examiner*—W. Gary Jones
*Assistant Examiner*—Kenneth R. Horlick
*Attorney, Agent, or Firm*—Felfe & Lynch

[57] ABSTRACT

A method for generating DNA probes specific for an organism and capable of distinguishing in a non-empirical manner between species. The method comprises amplifying, using a pair of oligonucleotide primers, a variable region of the genome of a number of phylogenetically related organisms to, or of a number of organisms suspected of being present in a given sample containing, said organism to be identified and having said variable region in its genome, at least one of said primers corresponding to a DNA sequence known or suspected of being conserved in said organisms, determining the sequence of the amplified region, selecting said sequence or a portion thereof to generate said probe specific for said organism to be identified by comparison with said other amplified regions and defining the hybridization conditions required to obtain a specific signal based on the precise nucleotide sequence of the selected probe. Specific probes are disclosed for a variety of species including *Aeromonas hydrophila*, *Aeromonas salmonicida*, *Clostridium difficile*, *Mycobacterium bovis*, *Mycobacterium tuberculosis* and *Salmonella typhimurium*.

11 Claims, 3 Drawing Sheets

ISOLATED NUCLEIC ACID MOLECULES TARGETED TO THE REGION INTERMIDIATE TO THE 16S AND 23S RRNA GENES USEFUL AS PROBES FOR DETERMINING BACTERIA

RELATED APPLICATION

This application is a divisional of U.S. patent application Ser. No. 07/830,465, filed Feb. 6, 1992 abandoned, which in turn is a continuation of U.S. patent application Ser. No. 07/510,853 filed Apr. 18, 1990 abandoned.

FIELD OF THE INVENTION

This invention relates to a method for generating DNA probes specific for an organism and capable of distinguishing between genera and species in a non-empirical manner.

BACKGROUND AND PRIOR ART

There are many situations where the identification of an organism in a sample is important. This is true in the analysis of clinical, veterinary, food and environmental samples. Currently it is possible to carry out such identification either by classical microbiological methods (where growth characteristics and/or biochemical parameters are monitored), by immunodiagnostic methods or by DNA-based methods.

DNA probes have been used for the identification of organisms as described for example in WO 89/06704 and U.S. Pat. No. 4,851,330. Many such probes derive from the observation (see Woese, Scientific American 244 (6) 1981 for review) that parts of the 16S and 23S ribosomal RNA (rRNA) sequences vary in different species. This information was used initially for phylogenetic analyses but it has more recently been used for DNA probe-based methods for the identification of organisms. The method by which the rRNA sequences which are characteristic of an organism were obtained depended initially on differential hybridization experiments in which the target DNA gave a positive signal and the organism from which it was required to be distinguished gave a negative signal or by procedures using hybridization experiments carried out in liquid in which sequences common to be both species are eliminated and sequences (which may be anonymous) which are unique to the organism of interest are retained. A final category of target sequences for DNA probes are regions of the genome which code for some antigen or biochemical product characteristic of the organism.

In all cases the success of the DNA probe depends on its ability to detect a target sequence in the organism of interest while it fails to hybridize to a panel of other organisms that are either closely related to the organism of interest or are likely to occur in the sample under study. Hybridization of a probe to target DNA depends on the DNA sequence and on the hybridization conditions used. There are well established guidelines for the selection of conditions which will allow DNA probes to distinguish between two very closely related sequences (Maniatis, T., et al. (1982) Cold Spring Harbor Publication). The design of DNA probes can be optimized if the DNA sequences targetted have maximum differences from those of other organisms and if a comprehensive data bank of DNA sequences in the region under study is available.

The DNA sequence of a segment of the genome of an organism can be obtained by isolating the DNA segment using a variety of techniques which are widely used by those that employ recombinant DNA methods (see Maniatis, T., et al. supra. More recently methods of amplification of the region of interest using methods such as the Polymerase Chain Reaction (PCR) (Saiki et al. (1985) Science 230 1350–1354) have been described.

The PCR technique requires two oligonucleotide primers that flank the DNA segment to be amplified. Repeated cycles of heat denaturation of the DNA, annealing of the primers to their complementary DNA sequences at a lower temperature, followed by extension of the annealed primer with a DNA polymerase, which may be thermostable, in the presence of the four deoxyribonucleotides gives rise to specific DNA sequences in sufficient quantities to be manipulated further.

In one use of the PCR method Chen, K., et al. (FEMS Microbiology Letters (1989) 57, 19–24) amplified *E. coli* using primers derived from the regions of the 16S rRNA gene which tend to be conserved in a variety of organisms examined. A similar approach has been used by Medlin, L., et al. Gene (1988) 71, 191–499) who amplified eucaryotic rRNA coding regions for a phylogenetic study.

The choice of a target sequence for a probe currently involves a) the identification of an area of sufficient interspecies diversity or variation that will allow for the provision of a specific probe and b) a target which is preferably present in the organism in a high number of copies. The rRNA gene products (16S and 23S) appear to fulfil both of these criteria and as such have been the target for many studies and, indeed, DNA probe kits directed to those regions are available commercially for some organisms. Most comparisons to date have been between the rRNA genes from different genera and these have highlighted a pattern of variable regions within the gene flanked by adjacent more conserved regions.

We have found that when related species are compared the "variable" regions are occasionally very similar (see Example 2), if not identical. This highlights the need for a method to obtain sequence data from a catalogue of organisms to allow one to select the correct probe sequence and the appropriate hybridization conditions or to identify regions of the genome of a microorganism in which greater variability occurs.

It is an object of the present invention to provide a method for obtaining DNA sequences which can be used to provide a DNA data base for the choice of probe and hybridization conditions in a rapid and useful manner.

It is a further object of the present invention to identify new target areas that contain a high degree of diversity between organisms and to generate highly specific DNA probes thereto in a variety of organisms of interest to the clinician, veterinary practitioner, the food technologist and the environmentalist.

SUMMARY OF THE INVENTION

Accordingly, the invention provides a method for generating a DNA probe specific for an organism to be identified and capable of distinguishing between genera and species in a non-empirical manner, said method comprising amplifying, using a pair of oligonucleotide primers, a variable region of the genome of a number of phylogenetically related organisms to, or of a number of organisms suspected of being present in a given sample containing, said organism to be identified and having said variable region in its genome, at least one of said primers corresponding to a DNA sequence known or suspected of being conserved in said organisms, determining the sequence of the amplified region, selecting said sequence or a portion thereof to generate said probe specific for said organism to be identified by comparison with said other amplified regions and defining the hybridization conditions required to obtain a specific signal based on the precise nucleotide sequence of the selected probe.

The method in accordance with the invention enables one to generate DNA probes which can discriminate between very closely related organisms. Thus the method according to the invention can distinguish between organisms in which only 2 bases are different at a given gene locus as hereinafter described.

The method according to the invention has universal application in the generation of DNA probes to variable regions of the genome of a given organism. The oligonucleotide primers may correspond to DNA sequences of conserved regions or portions thereof adjacent said variable region or portion thereof.

The method in accordance with the invention can be used to target an unknown region of the genome by rapidly establishing a DNA sequence data bank for that region for a number of organisms which are likely to be present in a sample and by deriving a DNA probe fragment which will identify the organism of interest under hybridization conditions determined by the sequence of the probe and the extent to which it differs from the other organisms. The method according to the invention represents a significant improvement over existing methods for identifying sequences useful as DNA probes.

DETAILED DESCRIPTION OF PREFERRED EMBODIMENTS

Because of the inadequacies in some cases of the 16S rRNA gene as a locus for DNA probing we have availed of the universality of the method in accordance with the invention to analyse other genomic regions for their ability to provide informative targets for DNA probes. We have searched in the first instance for regions that are least likely to be conserved. This consideration led us to focus attention on those regions of the genome which are intergenic, viz. spacers between functional genes as there should be minimal evolutionary pressure to conserve there regions.

Previous authors have published data on the intergenic region between the 16S and the 23S rRNA for *E. coli* (Brosius et al. J. Mol. Biol. 148 107–127 (1981)), *Streptomyces lividans* and *Mycobacterium bovis* BCG (Suzuki et al. J. Bact. 170 2886–2889 (1988)) and *Bacillus subtilis* (Green et al. Gene 37, 261–266 (1985)). Examination of these sequences by us has shown that there is a great variation between these unrelated genera.

In one aspect of the invention the variable region is a variable intergenic region and the primers correspond to conserved regions or portions thereof flanking said intergenic region. Thus as an example one of the primers may correspond to a conserved region of the 16S rRNA gene and the other primer may correspond to a conserved region of the 23S rRNA gene.

Alternatively, one of the primers may correspond to the conserved 3' end of the 16S rRNA gene and the other primer may correspond to the conserved 5' end of the 23S rRNA gene.

The primers can be derived from the available sequence data for 16S and 23S genes. When such primers are amplified in accordance with the invention using the PCR technique the amplified (intergenic) region can, in some situations, vary in size, such is the diversity between species, as hereinafter described.

By DNA sequencing such amplified regions additional detailed information on panels of microganisms has been obtained which has allowed DNA probes to be prepared which can distinguish between closely related organisms.

Although the intergenic region between the 16S and 23S genes is the target used in Example 1 other intergenic regions which are bounded by known sequences of functional genes can also be used as targets for DNA probes in accordance with the invention.

In the method according to the invention a conserved region of known sequence from another organism such as *E. coli* may be used to generate each said primer. A best fit sequence may be derived from known sequences from a number of organisms to generate each primer.

The amplification is preferably carried out by the PCR technique. The polymerase used is preferably a thermostable polymerase such as *Thermus aquaticus* (Taq) enzyme. It will be appreciated that zones of the genome of an organism which have been identified as target sequences for DNA probes in accordance with the invention may be isolated using methods other than PCR amplification.

Following amplification and prior to sequencing, the amplified nucleotide sequence may be ligated to a suitable vector followed by transformation of a suitable host organism with said vector. One thereby ensures a more readily available supply of the amplified sequence.

Alternatively, following amplification, the amplified sequence or a portion thereof may be chemically synthesized for use as a nucleotide probe. In either situation the DNA sequence of the variable region is established using methods such as the dideoxy method (Sanger, F. et al. Proc. Natl. Acad. Sci (1977) 74, 5463–5467). The sequence obtained is used to guide the choice of the probe for the organism and the most appropriate sequence(s) is/are selected.

We have determined that the DNA used for amplification may come from autoclaved samples. This is a particularly useful demonstration as it allows for ready preservation of samples and greater safety for laboratory workers.

The target organism is suitably a microorganism. For example, the organism may be selected from a species of Aeromonas, Bacillus, Clostridium, Enterococcus, Eschericia, Klebsiella, Mycobacterium, Pseudomonas, Salmonella Serratia, Staphylococcus or Streptococcus. Specific microbial species within these species include *Aeromonas caviae, Aeromonas hydrophila, Aeromonas media, Aeromonas salmonicida, Aeromonas sobria, Bacillus subtilis, Clostridium butyricum, Clostridium difficile, Clostridium pasteurianum, Clostridium perfringens, Clostridium tyrobutyricum, Eschericia coli, Enterococcus faecalis, Klebsiella pneumoniae, Mycobacterium avium, Mycobacterium bovis, Mycobacterium tuberculosis, Pseudomonas aeroginosa, Pseudomonas fluorescens, Salmonella typhimurium, Serratia mercescans, Staphylococcus aureus* and *Streptococcus pyogenes*.

The invention also provides specific probes obtainable by the preceding method.

The variable region targetted in accordance with the invention may be the V2 or V6 region of the gene coding for 16S rRNA. The V2 and V6 regions are two well characterised variable regions where frequently the greatest homology differences between species are observed. Using the V2 and V6 regions in accordance with the method of the invention two different probes can be generated for an organism of interest.

The invention provides a variety of probes for variable intergenic regions intermediate the genes coding for 16S rRNA and 23S rRNA and derived from the following sequences or sequences complementary thereto:

Clostridium difficile

AGAGAACCTGCCGTTGAATCACCTC-
CTTTCTAAGGAGAATAGAAAGAAGAAAATTCTTT
CTAAAGGCTGAATTCTCTGTT-
TAATTTTGAGAGACCATTCTCTCAAAAT-
TGAAACTTCT AATAAAATTGGGAAGTAGCTGAT-
CATCACCAAATCGTAAATTTTGGATGCCTAGCTACG
TTCTTTGAAAATTGCACAGTGAATAAAG-
TAAAGCTAAAGGTATATAAAAATCCTTTGTA AGAAT-
CAATTTAAGGTCAAGCTACAAAGGGCGCAT

Clostridium pasteurianum

AGAGAACCTGCCGGCTGGATCACCTC-
CTTTCTAAGGAGTAATTGTAGCAGGATAACTGT
TGTATACATTGGTTTCTTACTCT-
TGTCTCTGTTTAATTTTGAGAGATCAGTTCTCTTAA
GATGTACTTTGAAAATTGCATAGAGAAA-
CAAAGTAAAGTAAAAAATAATCCTTTGATAA TAT-
GATTTTAATCGAAAAGATTGAAATTAAA-
CAATAAAGACTAAACTCTAAAACGGGCT
AACGCCTAAAAGAGTAACAAGGTCAAGC-
TACAAAGGGCGCAT

Clostridium perfringens

AGGAGAACTGCGGCTGGATCACCTC-
CTTTCTAAGGAATACATCTTAGGACAACTAAGAT
GATAATGAATTCTGGATAATATCTCT-
GTTTAATTTTGAGAGACTATCTCTCAAAATTGT
TCTTTGAAAATTGCACATAATTTAATT-
TATAGAAACAACAAGCCAAATTGGCAAAACCA
ATTTCTATTCTTTGTAAAATGAGAAC-
TATAACTAATATAGGTCAAGCTACAAAGGGCGC AT

Mycobacterium avium

ACCGGAGGTGGGGCTGATCACCTCCTAT-
TCTAAGAGCACCACAAAACGACCCCGAACTG
GTGGGGTCGGGAGCCAGTAGGGGTTC-
CCGTCTAGTGACGGGGCCGGGTGCGCAACAGA
AATGATTGCCAGACACACTATTGGGC-
CCTGAGACAACACTCGGTCCGTCCGTGTGGAGT
CCCTCCATCTTGGTGGTGGGGTGTGGT-
GTTTGTATTGGGATAGTGGTTGCGATGATCTA GGT-
GAGCGCATGGTCTTCGTGGCCGGCCGT-
TGATCGAAATGGGTAATTTCTTTTTTAAC
TCTTGTGTGTAAGTAAGTGTTTAAGGGGGAT

Mycobacterium bovis

ACCGGAAAGGTCCGTGCGTGAAATT-
TAACCTTCCTTCCCTTTTCTAAGGAGCACCACGA
AAACGCCCCAACTGGTGGGCGTAGGCGT-
GAGGGGTTCTTGTCTGTAGTGGGCGAGACGG GGT-
GCATGACAACAAAGTTGCCACCAACA-
CACTGTTGGGTCCTGAGGCAACACTCGGAC
TTGTTCCAGGTGTTGTCCCCACCGCCT-
TGGTTGGTGGGGTGTGTGTTTGAGAACTGG
ATAGTGGTTGCAGCATCAATG-
GATACGCTGCCGGCTAGCGGTGGCGTGT-
TCTTTGTGC AATATTCTTTGGTTTTTGTTGTGTTTG-
TAAGTGTCTAAAGGGCGCAT

Mycobacterium tuberculosis

ACCGGAAGTCGTCGGGATCACCTC-
CTTTCTAAGGAGCACCACGAAAACGCCCCAACTGG
TGGGTCAGGCGTGAGGGGTTCTTGTCTG-
TAGTGGGCGAGACGGGGTGCATGACAACAAA
GTTGGCCACCAACACACTGTTGGATCCT-
GAGGCAACACTCGGACTTGTTCCAGGTGTTG
TCCCACCGCCTTGGTGGTGGGTGTGGT-
GTTTGAGAACGTGATAGTGGTTGCGAGCATCA ATG-
GATACCCGTGCCGGCTAGCGGTGGCGT-
GTTCTTTGTGCAATATCTTTGGTTTTTGT
TGTGTTTGTAAGTGTCTAAGGGCGCA

The above specifically mentioned probes are just some examples of specific probes which can be generated in accordance with the method of the invention.

To help satisfy the second requirement of DNA probes (i.e. high copy number) non-translated, transcribed regions have been chosen for analysis because these fulfil a functional role other than that of a messenger RNA which must be translated. Because of the usefulness of the intragenic regions of ribosomal genes other intragenic regions were investigated as being appropriate targets for DNA probes.

To allow us to define probes which can distinguish between related genera and species we have used the integrated method of the invention to rapidly define DNA probes for closely related organisms (see Example 2). In one demonstration of the method in which the intragenic region of the 16S rRNA was targeted we define a probe/hybridization conditions couple in which sequences differing only by 2 bases are distinguished.

To demonstrate the general usefulness of the method we have used available DNA sequences from E. coli to provide primers for a wide range of Gram positive, Gram negative, aerobic and anaerobic organisms.

Although the variable regions of the gene coding for 16S rRNA have been the basis of species-specific probes, the use of the constant regions as primers for PCR in accordance with the invention allows one to rapidly isolate that part of the gene coding for 16S rRNA from species on which no sequence or hybridization analysis has been performed. The subsequent DNA sequencing of the amplified region yields information on the variable part of the organism under study and this can be used as a DNA probe in subsequent experiments under defined conditions.

The invention provides a variety of probes for the V2 variable region of the gene coding for 16S rRNA and derived from the following nucleotide sequences or sequences complementary thereto:

Aeromonas hydrophila

GCTCAGATTGAACGCTGTCGGCAGGC-
CTAACACATGCAAGTCGAGCGGCAGCGGGAAAG
TAGCTTGCTATTTTGGGCGAGGCG

Aeromonas media

GCTCAGATTGAACGCTGGCGGCAGGGC-
CTAACACATGCAAGTCGAGCGGCAGACGGGAA
AGTAGCTTGCATACTTTTCCGGCGGAGCG

Aeromonas salmonicida

GCTCAGATTGAACGCTGGCGGCAGGC-
CTAACACATGCAAGTCGAGCGGCAGCGGGAAAG
TAGCTTGCTACTTTTGCCGGCGAGC

Aeromonas sobria

GCTCAGATTGAACGCTGGCGGCAGGC-
CTAACACATGCAAGTCGAGCGGCACGGGAAAGT
AGCTTGCTACTTTTGCCGGCGAGCG

Clostridium perfringens

GCTCAGCATGAACGCTGGCGGCGAGCT-
TAACACATGCAAGTCGAGCGATGAAGTTTCTT
CGGGAAATGGATTAGC

Eschericia coli

GCTCAGATTGAACGCTGGCGGCAGGC-
CTAACACATGAAGTCGAACGGTAACAGGAAGAA
GCTTGCTTCTTGGCTGACGAGT

Klebsiella pneumoniae

GCTCAGATTGAACGCTGGCGGCATGC-
CTAACACATGCAAGTCGCGGTACGACACAGAGC
TTGCTCTCGGGTGACGAGC

Mycobacterium bovis

GCTCAGGACGAACGCTGGCGGCGTGCT-
TAACACATGCAAGTCGAACGGAAAGGTCTCTT
CGGAGATACTCGAG

Pseudomonas fluorescens

GCTCAGATTGAACTGGCGGCAGGCCTAA-
CACATGCAAGTCGAGCGGTAGAGAGAAGCTT GCT-
TCTCTTGAGACG

Staphylococcus aureus

GCTCAGGATGAACTCTGGCGGCGAGC-
CTAATACATGCAAGTCGAGCGAACGGACGAGAA
GCTTGCTTCTCTGATGGTAGC

Salmonella typhimurium

GCTCAGATTGAACGTGGCGGCAGGC-
CTAACACATGCAAGTGCAACGGTAACAGGAAGCA
GCTCGTTCGCTGACGAGC.

The invention also provides a variety of probes for the V6 variable region of the gene coding for 16S rRNA and derived from the following nucleotide sequences or sequences complementary thereto:

Aeromonas hydrophila

TGGCCTTGACATGTCTGGAATCCTGCA-
GAGATGCGGGAGTGCCTTCGGGAATCAGAACA

Aeromonas media

TGGCCTTGACATCCAATGAACTTTCCA-
GAGATGGATTGGTGCCTTCGGGAACATTGAGA

Aeromonas salmonicida

TGGCCTTGACATGTCTGGAATCCTGTA-
GAGATACGGGAATCA

Aeromonas sobria

AGGTCTTGACATCCCGCTGCCCGCCTTA-
GAGATAAGGCTTTCTTCGGGGACAGCGTTG

Clostridium perfringens

TACTCTTGACATCCCTTGCATTACTCT-
TAATCGAGGAAATCCCTTCGGGGACAAG

Eschericia coli

TGGTCTTGACATCCACGGAAGTTTTCA-
GAGATGAGAATGTGCCTTCGGGAACCCT

Klebsiella pneumoniae

TGGTCTTGACATCCAGAGAACTTTCCA-
GAGATGGATTGGTGCCTTCGGGAACTGT

Mycobacterium bovis

TGGGTTTGACATGCACAGGACGCGTCTA-
GAGATAGGCGTTCCCTTGTGGCCT

Pseudomonas flourescens

AGGCCTTGACATCCAATGAACTTTCTA-
GAGATAGATTGGTGCTTCGGGAACATT

Staphylococcus aureus

AAATCTTGACATCCTTTGACAACTCTA-
GAGATAGAGCCTTCCCCTTCGGGACAAA

Salmonella typhimurium

TGGTCTTGACATCCACAGAACTTTCCA-
GAGATCGATTGGTGCTTCGGGAACTGT

The above specifically mentioned probes are some further examples of specific probes which can be generated in accordance with the method of the invention.

The data provided hereafter in Example 2 and above were based on sequences in the intragenic region of the 16S rRNA gene. Other RNA molecules that have a functional role other than that of a template for translation should also be useful as target sites for the generation of specific probes against RNAs which are present in high copy numbers. An example of such a transcribed but optionally translated gene region is the ribonuclease P component RNA (M1). A study of the published data (Bryan, D. James et al. (1988) Cell 52, 19–26) showed that there are variable regions within this RNA. We have demonstrated (Example 3) that effective primers can be prepared from the available data that will allow amplification of these variable regions. Using the methodology according to the invention one can derive a panel of DNA sequences of the amplified region and, using the method herein specified in accordance with the invention, develop DNA probes based on a comparison of the DNA sequences obtained.

The present invention enables the variable regions, be they intergenic or intragenic, to be analysed and to provide a DNA probe which will hybridize specifically under selected conditions to the chosen DNA.

Inherent in the method according to the invention is the selection of hybridization conditions appropriate for any given probe in a non-empirical manner. The hybridization conditions are selected on the basis of the precise nucleotide sequence of the probe which can be determined in a manner known per se for stable hybridization, so as to distinguish the sequence selected from that of closely related species as hereinafter further described in the Examples. The biochemical and physical parameters selected for optimal hybridization in any given situation are based on the ratio of A:T to G:C pairings involved in hybridization and modifying principally the temperature and salt concentration of the hybridization medium accordingly. Determination of the optimal hybridization conditions involves comparison of the amplified sequence with closely related sequences in an available or freshly created data bank, the latter having been created by the determination of previously unknown sequences in accordance with the invention. Thus the method according to the invention has both increased sensitivity due to the determination of optimal and controlled hybridization conditions and specificity due to the generation of species-specific probes appropriate to any region of the genome of an organism.

The method according to the invention provides for the generation of DNA probes for the detection of a variety of species of organisms and probes which can detect many members of given genera. The present invention provides a more general demonstration of target sites in organisms and thus represents an improvement on current targets for DNA probes and a logical and data based selection of DNA probe sequences and the conditions of hybridization under which they should be used.

The probes obtained in accordance with the method of the invention may be used for the detection and/or determination of an organism containing or suspected of containing a target nucleotide sequence by contacting said organism with said probe having a sequence complementary to said target sequence.

The applications of the above probes will be of benefit in a variety of situations. The probe for *Mycobacterium bovis*, for example, will provide a non-subjective test for the presence of this organism in cattle (or other species). Currently bovine T.B. is a disease of major economic importance in some European countries and in very many developing countries. The description of a probe for *Mycobacterium tuberculosis* will allow the detection of this fastidious organism in humans (currently it is undetected by standard microbiological procedures in 50% of clinically positive cases) and this is of growing importance as it occurs in about 20% of persons suffering from full-blown AIDS.

The probe for *Aeromonas salmonicida* will allow the detection in the environment or in fish of this pathogen which causes furunculosis with major economic losses in the salmon farming industry. The closely related organism *Aeromonas hydrophila* for which a probe is also described may cause diarrhoea and gastroenteritis if present in food. Finally, as further examples inter alia of the usefulness of these probes, the sequences provided for various clostridia will be of benefit in clinical analyses (e.g. *Clostridium difficile*) or the food industry.

The invention further provides a method of detecting a specific organism in a mixture of organisms, which method comprises determining the sequences of two selected nucleotide regions of said specific organism, at least one of said sequences being from a variable region of said organism, by a sequence of steps set forth in the method hereinbefore specified, and using said sequenced regions to generate a pair of primers to selectively amplify a specific nucleotide region of said organism and thereby detect said specific organism. The organism is suitably any one of those specifically hereinbefore mentioned.

It will be appreciated that the above method may comprise determining the sequences of two selected variable regions of a gene of the organism and using said sequenced variable regions to generate a pair of primers to selectively amplify a specific variable region of said gene and, thereby, generate a species-specific probe for said specific organism or, alternatively, to detect the product of amplification.

Accordingly, one can, for example, derive DNA sequences from the most variable region of the variable part of the rRNA gene. When two of these variable regions are obtained they can serve as very specific primers for the particular organism of interest. It will be appreciated the primers thus produced are equivalent to probes as hereinbefore described.

Alternatively, a combination of one species-specific primer as hereinbefore described and a constant or conserved region primer can be used in combination to specifically amplify the species of interest.

The selective amplification of the species of interest in the manner described above can further be confirmed by the use of a probe specific for the species. For example, in the case of the following specific organisms *Aeromonas salmonicida, Aeromonas hydrophila, Clostridium difficile, Clostridium perfringens, Staphylococcus aureus, Klebsiella pneumoniae, Pseudomonas fluorescens, Mycobacterium bovis* and *Salmonella typhimurium* probes for the V2/V6 can be readily identified by comparing the sequences for the relevant variable region given in Table 3a or Table 3b.

It will be appreciated that the methods according to the invention may be 'one-tube' methods involving minimal equipment and fewer manipulations than heretofore. Accordingly, the invention further provides any method hereinbefore specified wherein DNA preparation and amplification are carried out in a single tube.

The methods in accordance with the invention have application in animal, plant and microbial organisms. It will be appreciated that the probes prepared in accordance with the invention can be used as biosensors for a variety of applications.

Figure 1:
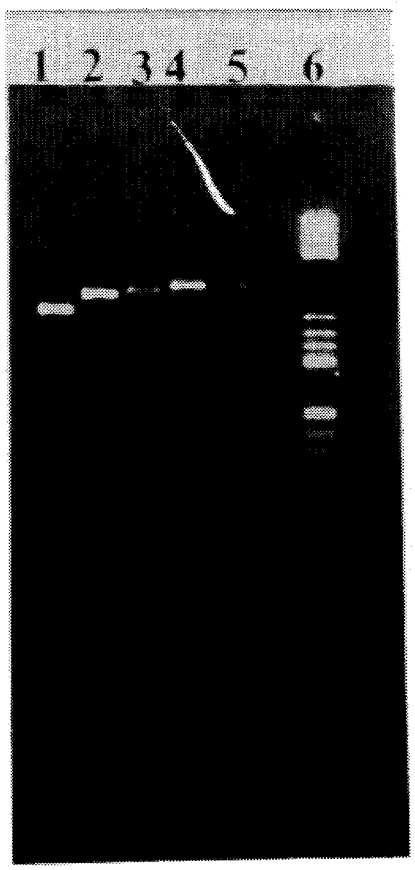
FIG. 1 is a photograph of an agarose gel amplified 16S–23S intergenic regions for Clostridium species prepared in Example 1.

The invention will be further illustrated by the following Examples.

EXAMPLE 1

General Procedure for the Isolation and PCR Amplification of DNA from Microorganisms: Illustration of Method applied to Intergenic Regions 50 µl ($10^5$–$10^6$ bacteria) of a fresh culture were pelleted by centrifugation at 10,000 r.p.m. for 1 min. in a bench top centrifuge and the supernatant discarded. The bacterial cultures were obtained from various laboratories in the Department of Microbiology, University College Galway, Ireland, University College Hospital, Galway, Ireland and the Veterinary College, University College Dublin, Ireland. The pellet was then resuspended in 25 μl of water. The sample was heated to 95° C. for 10 min. in a 750 μl Eppendorf tube, centrifuged briefly to remove condensation from the lid of the tube and then incubated in the presence of proteinase K (at a concentration of 50 μg/ml) at 55° C. for 15 min. Proteinase K was then denatured at 95° C. for 15 min. Condensation was again removed from the Eppendorf lid by a brief centrifugation and DNase free RNase A (Sigma) was added to a final concentration of 10 μg/ml and allowed to incubate for 15 min. at 37° C. to denature RNA. These incubations and reactions were carried out using a Perkin-Elmer-Cetus Thermo-cycler.

After RNA digestion, a 2×PCR reaction buffer (cocktail) (100 mm KCl, 20 mm Tris, pH 8.3, 3 mm $MgCl_2$, 0.2% gelatin, 400 μm dNTP, an appropriate concentration of primers (≅500 pmol of each for a 20 mer), and 2.5 units of Taq polymerase were added and 30 PCR cycles, in a final volume of 50 μl, were then carried out. Typically, a PCR cycle consists of DNA heat denaturation at 94° C. for 1 min., annealing of primers at 37° C.–55° C. for 2 min. and an extension reaction period at 72° C. for 1–3 min. The samples were allowed to cool to room temperature gradually and 1/10 (5 μl) of the reaction were analysed by gel electrophoresis on a 4% Nu-Sieve (Nu-Sieve is a Trade Mark) agarose minigel to determine the success of amplification (see FIGS. 1, 3 and 5).

Alternative methods using a combination of proteinase K, detergents, phenol extraction and ethanol precipitation can also be used successfully for the preparation of the DNA.

20-Mer oligonucleotide primers which come from the 3' end of the 16S rRNA gene and the 5' end of the 23S rRNA gene were synthesized on an Applied Biosystems or Beckman (Applied Biosystems and Beckman are Trade Marks) oligonucleotide synthesizer. The primers thus synthesized correspond to conserved sequences in those abovementioned regions as defined by Clustal Analysis (Higgins et al., Gene, 73 237–244 1988) of available 16S and 23S rRNA sequences.

The sequence of the 16S rRNA 3' primer is

5'                                3'
AGTCGTAACAAGGTAGCCGT

The sequence of the 23S rRNA 5' primer is:

5'                                3'
C T/G A/G C/T TGCCAA G/C GCATCCACC where "/" indicates a degenerate selection of a base at that position.

After deblocking, purification of the oligonucleotides was carried out by elution from preparative polyacrylamide gels, and purified further by chromatography on NAP10 columns.

PCR amplification with the above primers was carried out using the conditions outlined above for the following microorganisms: *Aeromonas caviae, Aeromonas hydrophila, Aeromonas salmonicida, Aeromonas sobria, Bacillus subtilis, Clostridium butyricum, Clostridium difficile, Clostridium pasteurianum, Clostridium perfringens, Clostridium tyrobutyricum, Escherichia coli, Enterococcus faecalis, Mycobacterium avium, Mycobacterium bovis, Mycobacterium tuberculosis, Pseudomonas aeroginosa, Serratia mercescans, Staphylococcus aureus* and *Streptococcus pyogenes*. The sizes of the amplified regions ranged from 200 to 650 base pairs. The data for the five Clostridium species are shown in FIG. 1 in which Lanes 1–6 represent the following:

Lane 1: *Clostridium perfringens* amplified 16S–23S rRNA intergenic regions

Lane 2: *Clostridium difficile* amplified 16S–23S rRNA intergenic regions

Lane 3: *Clostridium pasteurianum* amplified 16S–23S rRNA intergenic regions

Lane 4: *Clostridium butyricum* amplified 16S–23S rRNA intergenic regions

Lane 5: *Clostridium tyrobutyricum* amplified 16S–23S rRNA intergenic regions

Lane 6: pBR Hae III size markers

The PCR amplified DNA was subcloned into the vector M13 mp II by blunt end ligation into the SmaI site. The inserted DNA was sequenced by the Sanger dideoxy chain termination method. These operations were carried out by subjecting 50 ng of amplified DNA (approx. 20 μl of the PCR reaction) to drop dialysis against a 1000-fold volume of TE buffer (10 mM Tris, pH 8, 1 mM EDTA) for 2 h. The DNA was dried in a Heto-Vac (Heto-Vac is a Trade Mark) dessicator and then resuspended in 10 μl of ligation buffer containing 10 ng of SmaI digested M13 Mp 11 and one unit of T4 ligase. Ligation took place at 10° C. for at least 5 h. The DNA mixture was used to transform *E. coli* JM201. A single stranded DNA was prepared from recombinants for dideoxy sequencing using T7 polymerase. The DNA sequences that were obtained are set out above.

Figure 2:
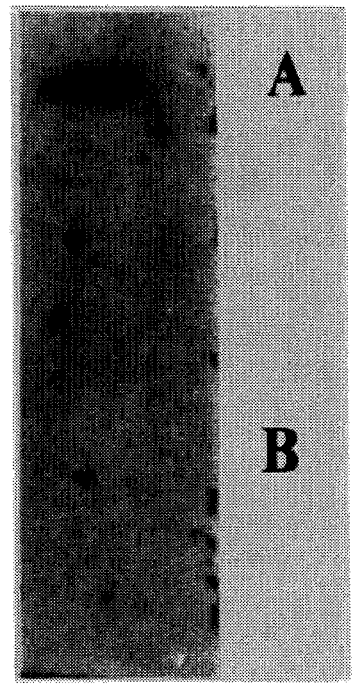
FIG. 2 is a photograph of an autoradiogram of hybridization of a DNA probe for the 16S–23S intergenic region of *Mycobacterium bovis* to *Mycobacterium bovis* and *Mycobacterium avium* DNA.

A clustal alignment of the Mycobacterium species sequences is shown in Table 1. The variable regions between them are indicated by a lower density of conserved bases (asterisk). Many possibilities for probe generation arise from this analysis. One fragment, 20b (which encompasses a 9b difference) underlined was selected (in Table 1) to demonstrate that *Mycobacterium bovis* can be distinguished from *Mycobacterium avium* (*Mycobacterium avium* is used as an indicator of non-pathogenic infections in cattle in current tests for bovine T.B.). When this sequence was radioactively labled by polynucleotide kinase (Amersham) in the presence of $\gamma^{32}PATP$ and used as a probe to the amplified intergenic regions of *Mycobacterium bovis* and *Mycobacterium avium* that had been slot blotted to a Nytran (Nytran is a Trade Mark) membrane (Schleiser and Schuell . . . ), the *Mycobacterium bovis* was detected whereas the *Mycobacterium avium* was not (FIG. 2). in FIG. 2 "A" corresponds to *Mycobacterium bovis* and "B" corresponds to *Mycobacterium avium*. The conditions for hybridization were 55° C. for 2 h. in 6×SSPE, 0.1% S.D.S. and washes were twice at room temperature in 6×SSC, 0.1% S.D.S. and once for 2 min. at 55° C. in 6×SSC 0.1% S.D.S. DNA sequences for Clostridium species obtained in a similar manner are shown in Table 2. Again the possibilities for DNA probes are obvious from the clustal analysis. An analysis of the sequences shown in Table 2 for three species of Clostridium show regions in which an identical series of sequences (indicated by asterisks) occurs which could serve as the basis of a genus specific probe for Clostridium, if required.

EXAMPLE 2

Amplification of V2 and V6 regions of microorganisms and probe generation therefrom.

Amplification was carried out in accordance with the procedures set out in Example 1. The 20 mer oligonucleotide primers which flank each side of the V2 (R1/R2) and V6 (U1/U2) variable regions of the 16S rRNA gene were selected from available data [Dams et al. Nucleic Acids Research Supplement 16 r87–r173 (1988)].

The primers thus synthesized had the following sequences:

```
    5'                           3'
R1: AATTGAAGAGTTTGATCATG

5'                           3'
R2: ACATTACTCACCCGTCCGCC

5'                           3'
U1: GCAACGGCGAAGAACCTTAC

5'                           3'
U2: GACAGCCATGCAGCACCTGT
```

Figure 3:
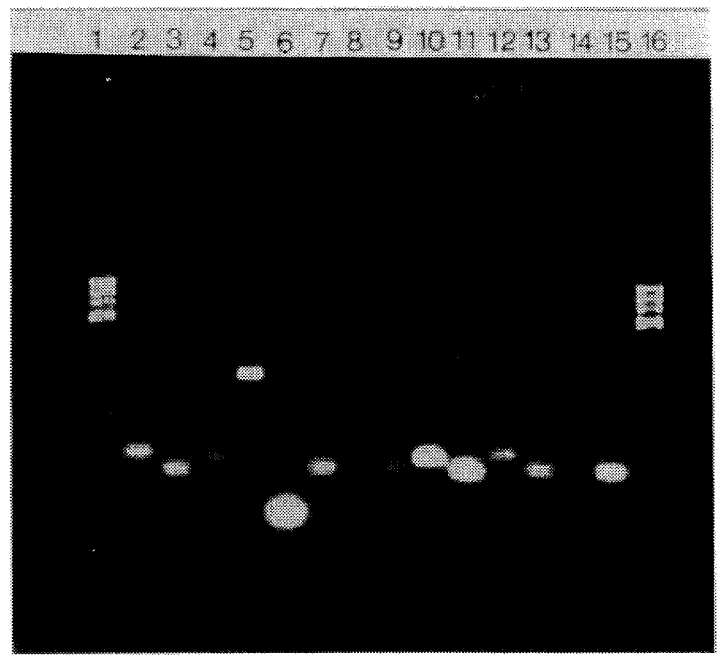
FIG. 3 is a photograph of an agarose gel of amplified 16S rRNA regions from a panel of organisms as prepared in Example 2.

PCR amplification with R1/R2 and U1/U2 as primers for V2 and V6, respectively, was carried out using the conditions outlined above for the following microorganisms: *Aeromonas salmonicida*, *Clostridium difficile*, *Klebsiella pneumoniae*, *Mycobacterium bovis*, *Pseudomonas fluorescens*, *Salmonella typhimurium* and *Staphylococcus aureus*. R1/R2 amplification of these species gave rise to approximately 120 base pair fragments in all cases analysed. U1/U2 primer amplification gave rise to an approximately 100 base pair fragment. FIG. 3 depicts the results obtained for R1/R2 primer V2 amplification and U1/U2 primer V6 amplification in which the lanes 1–16 represent the following:
Lane 1: pBR Hae III size markers.
Lane 2: *Aeromonas salmonicida* V2 amplification.
Lane 3: *Aeromonas salmonicida* V6 amplification.
Lane 4: *Clostridium difficile* V2 amplification.
Lane 5: *Clostridium difficile* V6 amplification.
Lane 6: *Klebsiella pneumoniae* V2 amplification.
Lane 7: *Klebsiella pneumoniae* V6 amplification.
Lane 8: *Mycobacterium bovis* V2 amplification.
Lane 9: *Mycobacterium bovis* V6 amplification.
Lane 10: *Pseudomonas fluorescens* V2 amplification.
Lane 11: *Pseudomonas fluorescens* V6 amplification.
Lane 12: *Salmonella typhimurium* V2 amplification.
Lane 13: *Salmonella typhimurium* V6 amplification.
Lane 14: *Staphylococcus aureus* V2 amplification.
Lane 15: *Staphylococcus aureus* V6 amplification.
Lane 16: pBR Hae III size markers.

The amplified bands indicate that the constant region primers are effective for Gram positive, Gram negative, aerobic and anaerobic organisms.

DNA sequences were obtained as described in Example 1. Examples of some of the DNA sequences obtained for both the V2 and V6 region are shown in Tables 3a and 3b. The sequences for the organisms other than *E. coli* were obtained using the methods herein described in accordance with the invention. The regions which correspond to the universal primers are boxed. The variable regions between them are indicated by a lower density of conserved bases (asterisk). A DNA probe specific for *Aeromonas salmonicida* selected on the basis of this analysis is indicated by a dashed line (Table 3b). This V6 probe sequence successfully distinguished *Aeromonas salmonicida* from *E. coli*, *Salmonella typhimurium*, *Clostridium difficile*, *Aeromonas hydrophila*, *Aeromonas media* and *Aeromonas caviae*, when these cultures were amplified using primers for the constant regions flanking V6 (see FIG. 4). It will be noted that the hybridization conditions used (hybridization was carried out at 57° C. for 2 h. in 6×SSPE, 0.1% SDS with the most stringent wash at 60° C. for 30 min. in 2×SSC) permitted the probe to distinguish between *A. salmonicida* and *A. hydrophila*, in which there is only a 2-base pair difference.

Figure 4:
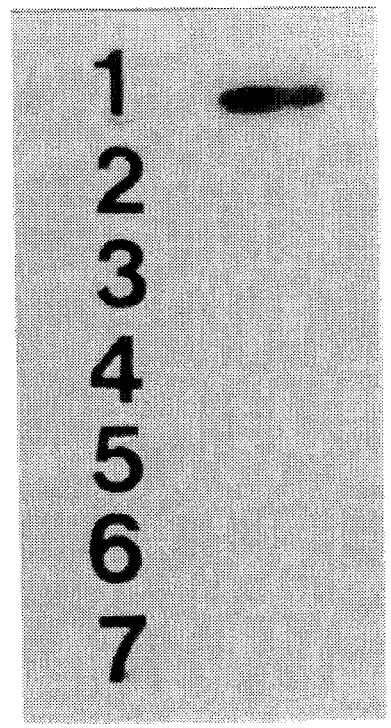
FIG. 4 is a photograph of an autoradiogram of hybridization of a DNA probe for 16S rRNA intragenic regions of *Aeromonas salmonicida* to a panel of organisms.

In FIG. 4 Lanes 1–7 represent the following:
Lane 1: *Aeromonas salmonicida*
Lane 2: *Aeromonas hydrophila*
Lane 3: *Aeromonas media*
Lane 4: *Aeromonas caviae*
Lane 5: *Escherichia coli*
Lane 6: *Salmonella typhimurium*
Lane 7: *Clostridium difficile*

EXAMPLE 3

Amplification of Variable Intragenic Regions of Ribonuclease P RNA Gene

Using the methods described in Examples 1 and 2, DNA primers selected as conserved from an analysis of published data (Bryan, D. James et al. (1988) supra) which flank the variable intragenic regions of ribonuclease P were synthesized. The sequences of the primers are:

synthesized. The sequences of the primers are: A 17-mer oligonucleotide

```
5'                                              3'
 G A/T C/T C A/G G A/G C/T A A/G TCGC T/C GC
``` and a 19-mer oligonucleotide

```
5'                                              3'
  C/T C G/T ATAAGCC G/A G/T GTT T/C TGT
```

Figure 5:
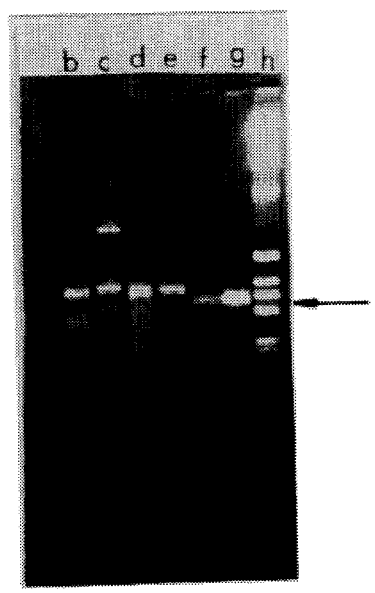
FIG. 5 is a photograph of an agarose gel of amplified ribonuclease P regions from a panel of organisms as prepared in Example 3.

These were used to amplify the corresponding intragenic regions in *Aeromonas salmonicida*, *Clostridium difficile*, *Clostridium pasteurianum*, *Escherichia coli*, *Enterococcus faecalis* and *Serratia mercescans*. The result (shown in FIG. 5) shows that both Gram positive, Gram negative, anaerobic and aerobic organisms can be amplified using these primers. In FIG. 5 Lanes b–h represent the following:
Lane b: *Escherchia coli*
Lane c: *Enterococcus faecalis*
Lane d: *Serratia mercescans*
Lane e: *Aeromonas salmonicida*
Lane f: *Clostridium pasteurianum*
Lane g: *Clostridium difficile*
Lane h: 1 kb ladder size marker.

The arrow indicates Ribonuclease P amplified DNA.

TABLE 1

```
Mycobacterium tuberculosis   ACCGGAA-  -GT C - GT- CG GGA-  - - TCACCTC C - - - - - - TTTCTAAGG AGCACCACGAAAACGCCCC-  AACTGGTGGGT
Mycobacterium bovis          ACCGGAAA G GT C C GTG CG TGAA A T T TAACCTT CCT T C C C T TTTCTAAGG AGCACCACGAAAACGCCCC-  AACTGGTGGGC
Mycobacterium avium          ACCGGAGG T G- - - GGG C- TGA- - - - TCACCT- - - - - - - CC T ATTCTAAG- AGCACCACAAAACGACCCCG AACTGGTGGGG
                             *******   *       *  *   **             *   ****                ********  ****           ***********

Mycobacterium tuberculosis   - CAGGCGTGAG- - - GGGTTCTTGTCTG T AGTGGGCGAGACGGGGTGCATGACAACAAAGTTGG CCAC C AACACACTGTTG
Mycobacterium bovis          G TAGGCGTGAG- - - GGGTTCTTGTCTG T AGTGGGCGAGACGGGGTGCATGACAACAAAGTTG- CCAC C AACACACTGTTG
Mycobacterium avium          T CGGGAGCCAGT A G GGGTTCCCGTCT- - AGTGACGGGGCCGGGTGCGCAACAGAAATGATTG CCA- - GACACACTATTG
                                   ****        ******  ****     ******** *  ****     ***           *** *  **     ******** ***

Mycobacterium tuberculosis   GATCCTGAGGCAACACTCGGA CTTGTT CCAGGTGTTGTCCC- A CCGCCTTGGT- GGTGGG- TGTG- GTGTTTGAG AACTG
Mycobacterium bovis          GGTCCTGAGGCAACACTCGGA CTTGTT CCAGGTGTTGTCCCC A CCGCCTTGGTT GGTGGGG TGTGT GTGTTTGAG AACTG
Mycobacterium avium          GGCCCTGAGACAACACTCGG-  TCCGT- CCGTGTGGAGTCCCT- CCATCTTGGT- GGTGGGG TGTG-  GTGTTTGT- ATTGG
                              ****** ************     **  *    ** **     ***       *** ****  ******  ****  *** *** ***    *

Mycobacterium tuberculosis   GATAGTGGTTGCGAGCATCAATGGATACCCG TGCC- - - - - - GGCTAGCGGTGGCGT GTT CTTT GT GC AAT AT - CTTT GGT
Mycobacterium bovis          GATAGTGGTTGCGAGCATCAATGGATACGC- TGCC- - - - - - GGCTAGCGGTGGCGT GTT CTTT GT GC AAT ATT CTTT GGT
Mycobacterium avium          GATAGTGGTTGCGATGATCTAGGTGAGCGCA TGGTC T T C GT GGCCGGCCGTTGATC G AAATGT GT AATTT CT TTTT AAC
                             *************  ***  *    **  *   **              * ******* *   *** *     *  **  *** *    *

Mycobacterium tuberculosis   TTGTTTT GTGTTTGTAAGTGTCTAA-  GGGCGC A-
Mycobacterium bovis          TTTTGTT GTGTTTGTAAGTGTCTAAA GGGCGC AT
Mycobacterium avium          TCTTGT-  GTGTAAGTAAGTGTTTAAG GGGGG-  AT
                             *  ****  ****  **********    ****    *
```

TABLE 2

| | |
|---|---|
| *Clostridium perfringens* | AGGAGAACTGC– GGC TGGATCACCTCCTTTCTAAGGAAT A– – CATCTTAGGACAACTAAGA TG– ATAA T GAA T T CTGGAT |
| *Clostridium difficile* | AGAGAACCTGCC GG– TGAATCACCTCCTTTCTAAGGAG– AA T AGAAAGAAGAAAATTCTT– TCT AAA– – GG– – – CTGAAT |
| *Clostridium pasteurianum* | AGAGAACCTGCC GGC TGGATCACCTCCTTTCTAAGGAGT AA T TGTAGCAGGATAACTGTTG TAT ACAT T GGT T T CTTACT |
| | * * **** ** ** ****************** * * ** ** * * * * * ** * |
| *Clostridium perfringens* | A A T A TCTCTGTTTAATTTTGAGAGACTA– – TCTCTCAAAATTGTTCTTTGAAA– – – – ATTGCACATAATT T AATTTA T AG– |
| *Clostridium difficile* | – – – – TCTCTGTTTAATTTTGAGAGACCA– T TCTCTCAAAATTGAAACTTCTAAT A A A ATTGGGAAGTAGC T GATCAT C ACC |
| *Clostridium pasteurianum* | C T T G TCTCTGTTTAATTTTGAGAGATCAG T TCTCTTAAGATGTACTTTGAAAAT T G C ATAGAGAAACAA– – AGTAA– – AGT |
| | ******************** * ***** ** ** * ** ** * * * * * |
| *Clostridium perfringens* | AAACAACAAGCCA– – – – – AATT G GCAAAACCAATT– – – – – – TCTATTCTTTGT AAAATGAG– – – – – AACTATAA– – – – – – C |
| *Clostridium difficile* | AAATCGTAAATTTT G G A T GCCT A GCTACGTTCTTTG A A A A T TGCACAGTGAAT AAAGTAAAG C T A A AGGTATATA A A A A T C |
| *Clostridium pasteurianum* | AAAAAATAATCCTT T G A T AAT– – ATGATTTTAATCG A A A A G ATTGAAATTAA– ACAATAAAG A C T A AACTCTAAA A C G G G C |
| | *** ** * * * * * * * * * ** * |
| *Clostridium perfringens* | TAATAT– – – – – – – – – – – – – – AGGTCAAGCTACAAAGGGCGCAT |
| *Clostridium difficile* | CTTTGTA A G A A T C A A T T – T A AGGTCAAGCTACAAAGGGCGCAT |
| *Clostridium pasteurianum* | TAACGCC T A A A A G A G T A A C A AGGTCAAGCTACAAAGGGCGCAT |
| | *********************** |

TABLE 3a

Multiple alignment of the DNA sequences of the V2 loop (region) of the gene coding for 16S rRNA of the following organisms: *Aeromonas salmonicida, Clostridium perfringens, Clostridium difficile, Salmonella typhimurium, Klebsiella pneumoniae. Pseudomonas fluorescens* and *Staphylococcus aureus* to the known *E. coli* V2 sequence.

Primer Region R1

| Organism | Sequence |
|---|---|
| *Escherichia coli* | A A TTGAAGAGTTTGATCATG GCTCAGATTGAAC G C TGGCGGCAGGCCTAACACATG- A A G T C G A A C G G T A A C A G G A A - G A A |
| *Aeromonas salmonicida* | A A TTGAAGAGTTTGATCATG GCTCAGATTGAAC G C TGGCGGCAGGCCTAACACATGC A A G T C G A G C G G C A G C G G G A A A G T A |
| *Clostridium perfringens* | A A TTGAAGAGTTTGATCATG GCTCAGGATGAAC G C TGGCGGCGAGTTAACACATGC A A G T C G A G C G A T - - - - - G A A |
| *Clostridium difficile* | A A TTGAAGAGTTTGATCATG GCTCAGGATGAAC G C TGGCGGCGTGCCTAACACATGC A A G T T G A G C G A T - - - - - - - - |
| *Salmonella typhimurium* | A A TTGAAGAGTTTGATCATG GCTCAGATTGAAC G - TGGCGGCAGGCCTAACACATGC A A G T C G A A C G G T A A C A G G A A - G C A |
| *Klebsiella pneumoniae* | A A TTGAAGAGTTTGATCATG GCTCAGATTGAAC G C TGGCGGCAGGCCTAACACATGC A A G T C G A G C G G T A C - - G A C A G A G A |
| *Pseudomonas fluorescens* | A A TTGAAGAGTTTGATCATG GCTCAGATTGAA- - C TGGCGGCAGGCCTAACACATGC A A G T C G A G C G G T A - - - - G A G A G A A |
| *Staphylococcus aureus* | - - TTGAAGAGTTTGATCATG GCTCAGGATGAACT C TGGCGGCGAGCCTAATACATGC A A G T C G A G C G A A C G - - G A C G A G A A |
|  | * * * * * * * * * * * * * * * * * * * * * * * * * * * * * * * * * * * * * * * * * * * * * * * * * * * * |

Primer Region R2

| Organism | Sequence |
|---|---|
| *Escherichia coli* | G C TTGCT- TCTTT GCT G - A C G A GT GGCGGACGGGTGAGTAATGT |
| *Aeromonas salmonicide* | G C TTGCTA CTTTT GCC G - G C G A GC GGCGGACGGGTGAGTAATGT |
| *Clostridium perfringens* | G - TTTCTT CGGGA AAT G G A TT A GC GGCGGACGGGTGAGTAATGT |
| *Clostridium difficile* | - - TTACTT CGGTA AA- - G A - - - GC GGCGGACGGGTGAGTAATGT |
| *Salmonella typhimurium* | G C TTGCT- CGGTC GCT G - A C G A GT GGCGGACGGGTGAGTAATGT |
| *Klebsiella pneumoniae* | G C TTGCT- CTCG- GGT G - A C G A GC GGCGGACGGGTGAGTAATGT |
| *Pseudomonas fluorescens* | G C TTGCTT CTCTT GA- - - - - G A GC GGCGGACGGGTGAGTAATGT |
| *Staphylococcus aereus* | G C TTGCTT CTCT- GAT G - - T T A GC GGCGGACGGGTGAGTAATGT |
|  | * * * * * * * * * * * * * * * * * * * * * * * * * * * |

*mean base conserved in all cases studied
-- indicates a gap which allows for optimal alignment

TABLE 3b

Multiple alignment of the DNA sequences of the V6 loop (region) of the gene coding for 16S rRNA of the following organisms: *Aeromonas salmonicida*, *Aeromonas hydrophilia*, *Clostridium perfringens*, *Clostridium difficile*, *Salmonella typhimurium*, *Klebsiella pneumoniae*, *Pseudomonas fluorescens* and *Staphylococcus aureus* to the known *E. coli* V6 sequence.

| | Primer Region U1 | | |
|---|---|---|---|
| *Escherichia coli* | GCAACGCGAAGAACCTTACC | TGGTCTTGACATCCACGGAAGT-TTTCAGAGATGAGAATGTGCCTTCGGGAACCC | T GA- G A |
| *Aeromonas salmonicida* | GCAACGCGAAGAACCTTACC | TGGCCCTTGACATGTCTGGAA-TCCTGTAGAGATA------CGGGAATCA | G AAC- A |
| *Aeromonas hydrophilia* | GCAACGCGAAGAACCTTACC | TGGCCCTTGACATGTCTGGAA-TCCTGCAGAGATG------CGGGAATCA | G AAC- A |
| *Clostridium perfringens* | GCAACGCGAAGAACCTTACC | TACTCTTGACATCCCTTGCATTACTCTCTTAATCGAGGAAAT-CCCTTCGGGGACAA | G GT- G A |
| *Clostridium difficile* | GCAACGCGAAGAACCTTACC | TAAGCTTGACATCCCAATGACATCTCCTTAATCGGA-GATCTTCTCGGGGACAT | T GGT G A |
| *Salmonella typhimurium* | GCAACGCGAAGAACCTTACC | TGGTCTTGACATCCACAGAACT-TTCCAGAGATGGATTGGTGC-TTCGGGAACTG | T GA- G A |
| *Klebsiella pneumoniae* | GCAACGCGAAGAACCTTACC | TGGTCTTGACATCCACAGAACT-TTCCAGAGATGGATTGGTGC-TTCGGGAACTG | T GA- G A |
| *Pseudomonas fluorescens* | GCAACGCGAAGAACCTTACC | AGGCCTTGACATCCAATGAACT-TTCTAGAGATAGATTGGTGC-TTCGGGAACAT | T GA- G A |
| *Staphylococcus aureus* | GCAACGCGAAGAACCTTACC | AAATCTTGACATCCTTTG-ACAACTCTAGAGATAGAGCCTTCCCCTTCGGGACAA | A GT- G A |
| | ******************** | * * * * * | * |

| | Primer Region U2 |
|---|---|
| *Escherichia coli* | CAGGTGCTGCATGGCT |
| *Aeromonas salmonicida* | CAGGTGCTGCATGGCT |
| *Aeromonas hydrophilia* | CAGGTGCTGCATGGCT |
| *Clostridium perfringens* | CAGGTGCTGCATGGCT |
| *Clostridium difficile* | CAGGTGCTGCATGGCT |
| *Salmonella typhimurium* | CAGGTGCTGCATGGCT |
| *Klebsiella pneumoniae* | CAGGTGATGCATGGCT |
| *Pseudomonas fluorescens* | CAGGTGGTGCATGGCT |
| *Staphylococcus aureus* | CAGGTGCTGCATGGCT |
| | ****** ********* |

*mean base conserved in all cases studied
– indicates a gap which allows for optimal alignment

What we claim is:

1. An isolated nucleic acid molecule, useful as a probe for specifically determining *Clostridium difficile* in the presence of other microorganisms, wherein said probe hybridizes to a variable intergenic region intermediate to the 16S and 23S rRNA genes of *Clostridium difficile* and is selected from the group consisting of (i) nucleotide sequence
AGAGAACCTGCCGTTGAATCACCTC-CTTTCTAAGGAGAATAGA AAGAAGAAAAT-TCTTTCTAAAGGCTGAATTCTCTGTTTAATTT TGAGAGACCATTCTCTCAAAAT-TGAAACTTCTAATAAAATTGG GAAGTAGCT-GATCATCACCAAATCGTAAATTTTGGAT-GCCTAG
CTACGTTCTTTGAAAATTGCACAGT-GAATAAAGTAAAGCTAA AGG-TATATAAAAATCCTTTGTAAGAAT-CAATTTAAGGTCAAG CTACAAAGGGCGCAT, (ii) the nucleotide sequence complementary to (i);

(iii) a portion of the nucleotide sequence (i) of sufficient length to specifically determine *Clostridium difficile* in the presence of other microorganisms, and (iv) the nucleotide sequence complementary to (iii).

2. An isolated nucleic acid molecule, useful as a probe for specifically determining *Clostridium pasteurianum* in the presence of other microorganisms, wherein said probe hybridizes to a variable intergenic region intermediate to the 16S and 23S rRNA genes of *Clostridium pasteurianum* and is selected from the group consisting of: (i) nucleotide sequence
AGAGAACCTGCCGGCTGGATCACCTC-CTTTCTAAGGAGTAATT GTAGCAGGATAACT-GTTGTATACATTGGTTTCTTACTCTTGTC TCT-GTTTAATTTTGAGAGATCAGTTCTCTTAAGAT-GTACTTTG AAAATTGCATAGAGAAACAAAG-TAAAGTAAAAAATAATCCTT TGATAATAT-GATTTTAATCGAAAAGATTGAAATTAAA-CAATA
AAGACTAAACTCTAAAACGGGCTAACGC-CTAAAAGAGTAACA AGGTCAAGCTA-CAAAGGGCGCAT, (ii) the nucleotide sequence complementary to (i);

(iii) a portion of the nucleotide sequence (i) of sufficient length to specifically determine *Clostridium pasteurianum* in the presence of other microorganisms, and (iv) the nucleotide sequence complementary to (iii).

3. An isolated nucleic acid molecule, useful as a probe for specifically determining *Clostridium perfringens* in the presence of other microorganisms, wherein said probe hybridizes to a variable intergenic region intermediate to the 16S and 23S rRNA genes of *Clostridium perfringens* and is selected from the group consisting of (i) nucleotide sequence
AGGAGAACTGCGGCTGGATCACCTC-CTTTCTAAGGAATACATC TTAGGACAAC-TAAGATGATAATGAATTCTGGATAATATCTCT GTTTAATTTTGAGAGACTATCTCT-CAAAATTGTTCTTTGAAAA TTGCACATAATT-TAATTTATAGAAACAACAAGCCAAATTGGC AAAACCAATTTCTATTCTTTGTAAAAT-GAGAACTATAACTAAT ATAGGTCAAGCTA-CAAAGGGCGCAT, (ii) the nucleotide sequence complementary to (i), (iii) a portion of the nucleotide sequence (i) of sufficient length to specifically determine *Clostridium perfringens* in the presence of other microorganisms, and (iv) the nucleotide sequence complementary to (iii).

4. An isolated nucleic acid molecule, useful as a probe for specifically determining *Mycobacterium avium* in the presence of other microorganisms, wherein said probe hybridizes to a variable intergenic region intermediate to the 16S and 23S rRNA genes of *Mycobacterium avium* and is selected from the group consisting of:

(i) nucleotide sequence
ACCGGAGGTGGGGCTGATCACCTCCTAT-TCTAAGCACCACA AAACGAC-CCCGAACTGGTGGGGTCGGGAGCCAG-TAGGGGTTC
CCGTCTAGTGACGGGGGCCGGGTGCG-CAACAGAAATGATTGC CAGACACACTAT-TGGGCCCTGAGACAACACTCGGTCCGTC-CGT
GTGGAGTCCCTCCATCTTGGTG-GTGGGGTGTGGTGTTTGTATT GGGATAGTG-GTTGCGATGATCTAGGTGAGCGCATG-GTCTTCG
TGGCCGGCCGTTGATCGAAATGGG-TAATTTCTTTTTTAACTCT TGTGTGTAAG-TAAGTGTTTAAGGGGGAT, (ii) the nucleotide sequence complementary to (i), (iii) a portion of the nucleotide sequence (i) of sufficient length to specifically determine *Mycobacterium avium* in the presence of other microorganisms, and (iv) the nucleotide sequence complementary to (iii).

5. An isolated nucleic acid molecule useful as a probe for specifically determining *Mycobacterium bovis* in the presence of other microorganisms, wherein said probe hybridizes to a variable intergenic region intermediate to the 16S and 23S rRNA genes of *Mycobacterium bovis* and is selected from the group consisting of:

(i) nucleotide sequence:
ACCGGAAAGGTCCGTGCGTGAAATT-TAACCTTCCTTCCCTTTT CTAAGGAGCAC-CACGAAAACGCCCCAACTGGTGGGCG-TAGGC
GTGAGGGGTTCTTGTCTGTAGTGGGC-GAGACGGGGTGCATGA CAACAAAGTTGC-CACCAACACACTGTTGGGTCCTGAG-GCAACA
CTCGGACTTGTTCCAGGTGTTGTC-CCCACCGCCTTGGTTGGTG GGGTGTGTGT-GTTTGAGAACTGGATAGTGGTTGCGAG-CATCA
ATGGATACGCTGCCGGCTAGCGGTG-GCGTGTTCTTTGTCAAT ATTCTTTG-GTTTTTGTTGTGTTTGTAAGT-GTCTAAAGGGCGCAT, and (ii) the nucleotide sequence complementary to (i).

6. An isolated nucleic acid molecule, useful as a probe for specifically determining *Mycobacterium tuberculosis* in the presence of other microorganisms, wherein said probe hybridizes to a variable intergenic region intermediate to the 16S and 23S rRNA genes of *Mycobacterium tuberculosis* and is selected from the group consisting of:

(i) nucleotide sequence:
ACCGGAAGTCGTCGGGATCACCTC-CTTTCTAAGGAGCACCACG AAAACGC-CCCAACTGGTGGGTCAGGCGTGAGGGGT-TCTTGTCT
GTAGTGGGCGAGACGGGGTGCATGACAA-CAAAGTTGGCCACC AACACACTGTTGGATC- CTGAGGCAACACTCGGACTTGTTCCAG GTGTTGTCCCACCGCCTTGGTGGTGGGT-GTGGTGTTTGAGAAC GTGATAGTGGTTGC-GAGCATCAATGGATACCCGTGCCGGCTA GCGGTGGCGTGTTCTTTGTG-CAATATCTTTGGTTTTTGTTGTG TTTG-TAAGTGTCTAAGGGCGCA, (ii) the nucleotide sequence complementary to (i), (iii) a portion of the nucleotide sequence (i) of sufficient length to specifically determine *Mycobacterium tuberculosis* in the presence of other microorganisms, and (iv) the nucleotide sequence complementary to (iii).

7. The isolated nucleic acid molecule of claim 1, consisting of nucleotide sequence:

AGAGAACCTGCCGTTGAATCACCTC-CTTTCTAAGGAGAATAGA AAGAAGAAAAT-TCTTTCTAAAGGCTGAATTCTCTGTTTAATTT TGAGAGACCATTCTCTCAAAAT-TGAAACTTCTAATAAAATTGG GAAGTAGCT-GATCATCACCAAATCGTAAATTTTGGAT-GCCTAG CTACGTTCTTTGAAAATTGCACAGT-GAATAAAGTAAAGCTAA AGG-TATATAAAAATCCTTTGTAAGAAT-CAATTTAAGGTCAAG CTACAAAGGGCGCAT, or the nucleotide sequence complementary thereto.

8. The isolated nucleic acid molecule of claim 2, consisting of nucleotide sequence:

AGAGAACCTGCCGGCTGGATCACCTC-CTTTCTAAGGAGTAATT GTAGCAGGATAACT-GTTGTATACATTGGTTTCTTACTCTTGTC TCT-GTTTAATTTTGAGAGATCAGTTCTCTTAAGAT-GTACTTTG AAAATTGCATAGAGAAACAAAG-TAAAGTAAAAAATAATCCTT TGATAATAT-GATTTTAATCGAAAAGATTGAAATTAAA-CAATA AAGACTAAACTCTAAAACGGGCTAACGC-CTAAAAGAGTAACA AGGTCAAGCTA-CAAAGGGCGCAT, or the nucleotide sequence complementary thereto.

9. The isolated nucleic acid molecule of claim 3, consisting of nucleotide sequence:

AGGAGAACTGCGGCTGGATCACCTC-CTTTCTAAGGAATACATC TTAGGACAAC-TAAGATGATAATGAATTCTGGATAATATCTCT GTTTAATTTTGAGAGACTATCTCT-CAAAATTGTTCTTTGAAAA TTGCACATAATT-TAATTTATAGAAACAACAAGCCAAATTGGC AAAACCAATTTCTATTCTTTGTAAAAT-GAGAACTATAACTAAT ATAGGTCAAGCTA-CAAAGGGCGCAT, or the nucleotide sequence complementary thereto.

10. The isolated nucleic acid molecule of claim 4, consisting of nucleotide sequence:

ACCGGAGGTGGGGCTGATCACCTCCTAT-TCTAAGAGCACCACA AAACGAC-CCCGAACTGGTGGGGTCGGGAGCCAG-TAGGGGTTC CCGTCTAGTGACGGGGGCCGGGTGCG-CAACAGAAATGATTGC CAGACACACTAT-TGGGCCCTGAGACAACACTCGGTCCGTC-CGT GTGGAGTCCCTCCATCTTGGTG-GTGGGGTGTGGTGTTTGTATT GGGATAGTG-GTTGCGATGATCTAGGTGAGCGCATG-GTCTTCG TGGCCGGCCGTTGATCGAAATGGG-TAATTTCTTTTTTAACTCT TGTGTGTAAG-TAAGTGTTTAAGGGGGGAT, or the nucleotide sequence complementary thereto.

11. The isolated nucleic acid molecule of claim 6, consisting of nucleotide sequence:

ACCGGAAGTCGTCGGGATCACCTC-CTTTCTAAGGAGCACCACG AAAACGC-CCCAACTGGTGGGTCAGGCGTGAGGGGT-TCTTGTCT GTAGTGGGCGAGACGGGGTGCATGACAA-CAAAGTTGGCCACC AACACACTGTTGGATC-CTGAGGCAACACTCGGACTTGTTCCAG GTGTTGTCCCACCGCCTTGGTGGTGGGT-GTGGTGTTTGAGAAC GTGATAGTGGTTGC-GAGCATCAATGGATACCCGTGCCGGCTA GCGGTGGCGTGTTCTTTGTG-CAATATCTTTGGTTTTTGTTGTG TTTG-TAAGTGTCTAAGGGCGCA, or the nucleotide sequence complementary thereto.

* * * * *